United States Patent

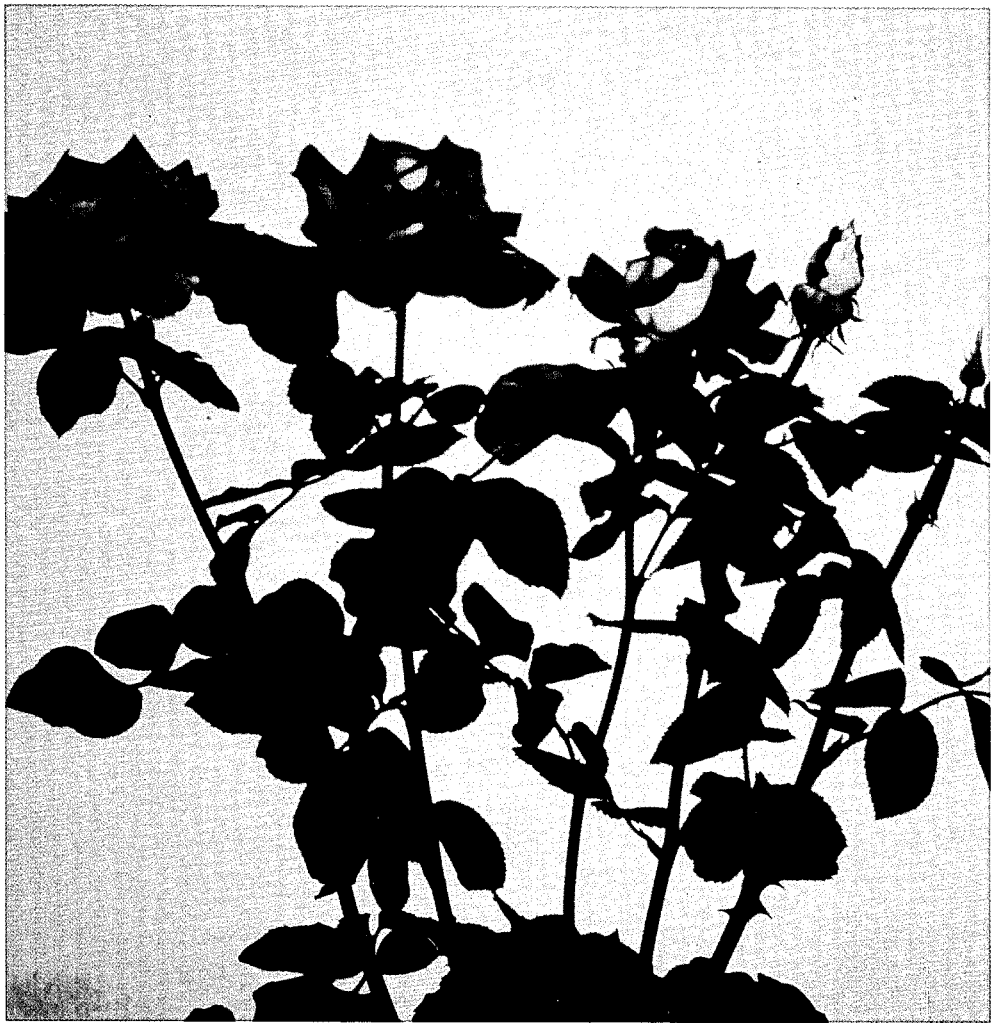

Plant Pat. 3,822

Patented Dec. 23, 1975

1

3,822

ROSE PLANT

Samuel D. McGredy, P.O. Box 14-100, Panmure, Auckland, New Zealand

Filed Oct. 16, 1974, Ser. No. 514,771

Int. Cl. A01h 3/00

U.S. Cl. Plt.—12 1 Claim

The present invention relates to a new and distinct variety of rose plant of the hybrid tea class, which was originated by my crossing the rose variety known as "Red Lion" with the rose variety known as "Hanne."

Among the novel characteristics possessed by this new variety which distinguish it from its parents and all other varieties of which I am aware are: (1) flowers of bicolor tonality which combine a red color on the obverse of the petals with yellow, silver-white and red tones on the reverse, (2) flowers of high center and spiral form which are very long lasting on the plant, (3) large foliage of leathery texture, and (4) few thorns, irregular and scattered. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "45B" is plate 45B of the Royal Horticultural Society Colour Chart.

Parentage: Seedling
- Seed parent: "Red Lion"
- Pollen patent: "Hanne"

Class: Hybrid tea

The following observations are made of specimens grown outdoors at Clackamas County, Oreg., during the month of July.

1. FLOWER

Blooming habit: Continuous

A. Bud
- (1) Size: Medium.
- (2) Form: Initially ovoid then high centered, petals spiralled.
- (3) Color: When sepals first divide: Bicolored 45B obverse/10A reverse. When petals begin to unfurl: Bicolored 45C obverse/49C reverse. When half-blown: Bicolored 51A obverse/49D reverse.
- (4) Sepals: Glabrous ornate. Color: Inside—150B; outside—149A. Overlay—48A; overlay—60B.
- (5) Calyx: Color—141D; shape—flattened; size—small to average; aspect—upright glabrous; odor when rubbed—faint rose.
- (6) Peduncle: Length—1½" to 1⅞"; aspect—glabrous; strength—medium to stout; color—175A.

B. Bloom
- (1) Size: Average size when fully expanded—5½ to 6 inches.
- (2) Borne: Singly.
- (3) Form: High center spiralled strongly reflexed.
- (4) Petalage: Number of petals under normal conditions—20 to 24.
- (5) Color: Center of flower—45B; outer petals—45C; base of petals—14B; inside of petals—45C; reverse of petals—49C; general tonality from a distance—45C.

2

C. Petals
- (1) Texture: Thick—crisp.
- (2) Appearance: Satiny surface, flat reverse.
- (3) Form: Spiralled.
- (4) Arrangement: Regular.
- (5) Petaloids in center: Medium—petalaceous.
- (6) Persistence: Drop clean.
- (7) Fragrance: Slight—sweet.
- (8) Lasting quality: Very long lasting on plant opening fairly rapidly when cut.

2. REPRODUCTIVE ORGANS

A. Stamens, anthers: Small
- (1) Arrangement: Regular.
- (2) Color: Yellow.

B. Stamens, filaments (threads): Short
Color: Yellow

C. Pollen: Color—Yellow

D. Styles: Medium length, uniform

E. Stigmas: Color—45A

F. Ovaries: 80 to 90

G. Hips:
Shape: Round—flattened.
Color: 2A to 4B when mature.

A. Form: Almost fastigate in appearance, canes long, strong and upright

B. Growth: Very vigorous and upright; height attained—5 ft.

C. Foliage: 5 to 7 parted, lustrous and leathery
- (1) Size: Large.
- (2) Quantity: Abundant.
- (3) Color: New foliage: upper side—187B; underside—59C. Old foliage; upper side—139A; underside—138B.
- (4) Shape: Oval—pointed.
- (5) Texture: Upper side—leathery; underside—stippled.
- (6) Edge: Doubly serrate.
- (7) Serration: Double.
- (8) Leaf stem: Color—166A; underside—145A.
- (9) Stipules: Medium, slightly serrate.

D. Wood
- (1) New wood: Color—146C; bark—smooth with waxy bloom.
- (2) Old wood: Color—137B; bark—waxy smooth.

E. Thorns
- (1) Thorns: Quantity: on main stalks from base—few except at base; on laterals from stalk—few except at base; form—recurved; length—large; color (when young)—53C; position—irregular, scattered.
- (2) Prickles: Quantity: on main stalks—few; on laterals—nearly absent.
- (3) Short needles: Quantity: few at base; on main stalks—few; on laterals—nearly none.

F. Plant's disease resistance:
Mildew—good.
Blackspot—good.
Rust—good.

I claim:

1. A new and distinct variety of rose plant of the hybrid tea class, substantially as shown and described, characterized particularly by flowers of unique bicolor tonality combining red obverse coloring of the petals with yellow, silver-white and red tones on the reverse and high center, spiral formation of petals that unfurl spirally during the development period and by a plant of tall, upright habit of growth having an abundance of large, leathery, lustrous leaves which are reddish to purple when young and dark green when mature.

No references cited.

ROBERT E. BAGWILL, Examiner